United States Patent [19]

Gressel et al.

[11] Patent Number: 4,966,773
[45] Date of Patent: Oct. 30, 1990

[54] TOPICAL OPHTHALMIC COMPOSITIONS CONTAINING MICROFINE RETINOID PARTICLES

[75] Inventors: Philip D. Gressel, Everman; Robert E. Roehrs, Fort Worth, both of Tex.; John L. Ubels, Milwaukee; Henry F. Edelhauser, New Berlin, both of Wis.

[73] Assignee: Alcon Laboratories, Inc., Fort Worth, Tex.

[21] Appl. No.: 339,915

[22] Filed: Apr. 17, 1989

Related U.S. Application Data

[63] Continuation of Ser. No. 934,768, Nov. 25, 1986, abandoned, which is a continuation-in-part of Ser. No. 711,419, Mar. 13, 1985, abandoned.

[51] Int. Cl.$^5$ .................. A61K 9/14; A61K 31/13; A61K 31/20; A61K 31/045
[52] U.S. Cl. .................. 424/489; 424/78; 514/559; 514/693; 514/724; 514/912; 514/915
[58] Field of Search ............... 514/724, 559, 693, 912, 514/915; 424/489, 78

[56] References Cited

U.S. PATENT DOCUMENTS

| | | | |
|---|---|---|---|
| 3,506,760 | 4/1970 | Brod | 424/253 |
| 3,828,777 | 8/1974 | Ness | 128/260 |
| 3,843,782 | 10/1974 | Krezanoski et al. | 424/78 |
| 3,920,810 | 11/1975 | Rankin | 424/80 |
| 3,987,163 | 10/1976 | Rankin | 424/78 |
| 4,039,662 | 8/1977 | Hecht et al. | 424/180 |
| 4,131,651 | 12/1978 | Shah et al. | 424/78 |
| 4,219,545 | 8/1980 | Collins | 424/81 |
| 4,247,547 | 1/1981 | Marks | 514/179 |
| 4,421,748 | 12/1983 | Trager et al. | 424/78 |

FOREIGN PATENT DOCUMENTS

| | | |
|---|---|---|
| 844544 | 1/1977 | Belgium . |
| 0077197 | 4/1983 | European Pat. Off. . |
| 1431841 | 9/1973 | United Kingdom . |
| 1430223 | 3/1976 | United Kingdom . |

OTHER PUBLICATIONS

Chem. Abst. 86: 111126(r) (1977)–List et al.
Arvo–1984–Ubel et al.,–3–9:00–"Vitamin A is Present as Retinol in Tears", Dispersa-Theapeutic Index–Feb. 1981.
Tseng, "Topical Vitamin A Treatment for Dry Eye Disorders", Science Writers Seminar in Ophthalmology, 9-30-10-3, Research to Prevent Blindness, pp. 1-6 (1984).
Sommer et al., "Topical Retinoic Acid in the Treatment of Corneal Xerophthalmia", Am. Journal of Ophthalmology, vol. 86, pp. 615-617 (1978).
Van Horn et al., "Topical Retinoic Acid in the Treatment of Experimental Xerophthalmia in the Rabbit", Archives of Ophthalmology, vol. 99, pp. 317-321, 1981.
Pirie, "Effects of Locally Applied Retinoic Acid on Corneal Xerophthalmia in the Rat", Experimental Eye Research, vol. 25, pp. 297-302 (1977).
Ubels et al., "Healing of Experimental Corneal Wounds Treated with Topically Applied Retinoids", Am. Journal of Ophthalmology, vol. 95, pp. 353-358 (1983).
Smolin et al., "Tretinoin and Corneal Epithelial Wound Healing", Archives of Ophthalmology, vol. 97, pp. 545-546 (1979).
Hatchell et al., "Treatment of Xerophthalmia with Retinol, Tretinoin and Etretinate", Archives of Ophthalmology, vol. 102, pp. 926-927 (1984).
Grosz, "Local Use of Vitamin A Preparation in Ophthalmic Practice", Archives of Ophthalmology, vol. 5, pp. 727-734 (1939).
Sommer, "Treatment of Corneal Xerophthalmia with Topical Retinoic Acid", Am. Journal of Ophthalmology, vol. 95, pp. 349-352 (1983).
Hatchell et al., "Corneal Epithelial Wound Healing in Normal and Diabetic Rabbits Treated with Tretinoin", Archives of Ophthalmology, vol. 103, pp. 98-100 (1985).
Tseng et al., "Topical Retinoid Treatment for Various Dry-Eye Disorders", Ophthalmology, vol. 92, pp. 718-727 (1985).

Primary Examiner—Douglas W. Robinson
Assistant Examiner—Zohreh A. Fay
Attorney, Agent, or Firm—James Arno; Gregg Brown

[57] ABSTRACT

Topical ophthalmic compositions containing microfine particles of one or more retinoids are described. The compositions are useful in the treatment of dry eye syndrome and related ophthalmic surface disorders and as ocular lubricants. A method of treating dry eye syndrome and related ophthalmic surface disorders and a method of providing topical ocular lubrication using these compositions are also described.

7 Claims, No Drawings

TOPICAL OPHTHALMIC COMPOSITIONS CONTAINING MICROFINE RETINOID PARTICLES

This is a continuation of application Ser. No. 934,768, filed Nov. 25, 1986, which is a continuation-in-part of Ser. No. 711,419 filed Mar. 13, 1985 both now abandoned.

BACKGROUND OF THE INVENTION

1. Field of the Invention

The present invention relates to topical ophthalmic compositions which act as ocular lubricants and are useful in the treatment of dry eye syndrome and related disorders. These compositions comprise microfine particles of one or more retinoids, and a suitable ophthalmic vehicle.

2. Discussion of Related Art

The problems associated with dry eye syndrome and related eye ailments associated with inadequate lubrication of the eye have been the subject of considerable discussion in the scientific and patent literature. For example, these problems are discussed in U.S. Pat. Nos. 4,131,651; 4,039,662; 3,987,163; 3,920,810; and 3,843,782; and Belgian Patent No. 844,544. The contents of these patents relating to dry eye syndrome and related surface disorders are incorporated herein by reference.

The above-cited patents disclose formulations which are said to relieve the symptoms associated with dry eye syndrome. However, none of these prior art formulations meet all of the important criteria for an effective and long lasting treatment of dry eye syndrome, particularly the moderate to serve keratoconjunctivitis sicca (KCS) patient. These prior art attempts fall into three categories corresponding to their physical state: liquids, anhydrous ointments, and solids. The solids are in the form of ocular inserts which slowly dissolve or erode to provide a thickened tear film. While these have the potential for providing longer term symptomatic relief than liquids, few patients are willing to persist in using them since they are difficult to insert and, once in place, tend to be uncomfortable, frequently themselves causing the foreign body sensation they were meant to treat. Prior liquid and ointment formulations, while giving the sensation of relief, are strictly palliatives without long-term effect.

A further description of the physical manifestations associated with dry eye disorders is seen in a scientific paper presented by Scheffer Chuei-Goong Tseng at the Science Writers Seminar in Ophthalmology, sponsored by Research to Prevent Blindness, Inc., held in Washington, DC, Sept. 30 to Oct. 3, 1984: Tseng, "Topical Vitamin A Treatment for Dry Eye Disorders," pages 1-6 (1984). The Tseng article describes experiments in which an ointment containing Vitamin A is utilized to treat dry eye disorders associated with Sjogrens's Syndrome and Stevens-Johnson Syndrome.

Still further description concerning dry eye disorders is presented in U.S. patent applications Ser. Nos. 700,861 and 695,364 filed Jan. 23, 1985, which are based on International Applications Nos. PCT/US83/00841 and PCT/US83/00840 filed May 25, 1983, respectively; the entire contents of these applications are incorporated herein by reference. These applications are directed to the use of ophthalmic solutions and gels based on polyanionic polymers for the treatment of dry eye disorders. The preparations of the present invention differ from the solutions and gels described in these related applications in that, inter alia, the preparations of the present invention contain microfine particles of one or more retinoids.

Certain retinoids have been previously identified as being useful in the treatment of various ophthalmic disorders. For example, U.S. Pat. No. 3,506,760 discloses oral compositions containing caffeine and beta-carotene (10,000 to 100,000 International Units of Vitamin A activity), and indicates that oral administration of theses compositions provides an effective treatment for night blindness. British Patent Specification No. 1,430,223 discloses topical anti-inflammatory preparations which contain a steroid as a principal active ingredient, along with other ingredients such as antimicrobial and keratolytic agents; retinoic acid is disclosed as a possible keratolytic agent. This patent does not provide any teaching concerning the use of retinoids in ocular lubricant preparations for treating dry eye syndrome and related ophthalmic surface disorders. British Patent Specification No. 1,431,841 discloses the use of ophthalmic-nutritional preparations for the treatment of ophthalmic disorders caused by a Vitamin A deficiency. These preparations contain Vitamin A and other vitamins, and are indicated as being useful when taken orally or applied topically. This reference does not provide any teaching concerning ocular lubricants suitable for the topical treatment of dry eye syndrome. European Patent Application No. EP 0 077 197 A1 discloses the use of retinoic acid in combination with methotrexate to prevent proliferation of remnant lens epithelial cells.

The use of topically applied retinoic acid in the treatment of xerophthalmia, an ophthalmic disorder caused by Vitamin A deficiency and characterized by a dryness of the conjunctiva and cornea, is discussed in the following articles: Sommer, et al., "Topical Retinoic Acid in the Treatment of Corneal Xerophthalmia," *American Journal of Ophthalmology*, Vol. 86, pages 615-617 (1978); Van Horn, et al., "Topical Retinoic Acid in the Treatment of Experimental Xerophthalmia in the Rabbit," *Archives of Ophthalmology*, Vol. 99, pages 317-321 (1981); and Pirie, "Effects of Locally Applied Retinoic Acid on Corneal Xerophthalmia in the Rat," *Experimental Eye Research*, Vol. 25, pages 297-302 (1977). These articles discuss the use of topical retinoic acid therapy in conjunction with systemic administration of Vitamin A to treat xerophthalmia. This discussion does not indicate that topically applied retinoids alone would be effective in the treatment of dry eye disorders and as ocular lubricants. Furthermore, these articles do not offer any solutions to the formulatory problems addressed by the present invention; more specifically, these articles do not disclose or suggest the use of microfine retinoid particles in order to avoid the solubility and crystal irritation problems commonly associated with retinoids.

The use of topically applied retinoids to promote healing of corneal wounds is discussed in the following article: Ubels, et al., "Healing of Experimental Corneal Wounds Treated with Topically Applied Retinoids," *American Journal of Ophthalmology*, Vol. 95, pages 353-358 (1983). This discussion indicates that the retinoids were dissolved in ethanol and then combined with corn oil. The final formulations are described as solutions which contain "not more than 2% ethanol in corn oil." This article also fails to offer any solutions to the formulation problems addressed by the present invention. Moreover, it is believed that the use of ethanol to solubilize the retinoids and consequent presence of ethanol in the solutions would tend to aggravate most dry eye disorders and counteract any lubricating effect of the solutions.

Three prior art problems associated with ophthalmic compositions containing one or more retinoids have been the poor solubility of retinoids, the instability of pharmaceutical compositions containing these compounds, and the irritation frequently associated with topical application of these compositions to the eye. The present invention is directed to solving these and other problems.

Summary of the Invention

A principal object of the present invention is the provision of topical ophthalmic compositions which are useful in treating the symptoms associated with dry eye syndrome and related ophthalmic surface disorders, and which have a topical ocular lubricating effect.

Another object of the present invention is the provision of a method for treating dry eye syndrome and related ophthalmic surface disorders and a method of providing topical lubrication to the eye.

The foregoing objects and other general objects of the present invention are satisfied by the provision of topical ophthalmic compositions comprising an effective amount of one or more retinoids in microfine particle form and a suitable ophthalmic vehicle. The present invention also provides a method of treating dry eye syndrome and related ophthalmic surface disorders and a method of providing topical lubrication to the eye utilizing such compositions.

Detailed Description of the Invention

The topical ophthalmic compositions of the present invention comprise an effective amount of one or more retinoids as a principal active ingredient, and a pharmaceutically acceptable ophthalmic vehicle. More particularly, the compositions of this invention comprise an effective amount of one or more retinoids in microfine particle form dispersed in a pharmaceutically acceptable ophthalmic vehicle. The one or more retinoids are contained in the present compositions in an amount of from about 0.00001% to about 0.01% by weight and preferably in an amount of from about 0.00001% to about 0.001% by weight. It has been discovered that even very low concentrations in these ranges are effective in treating dry eye syndrome and providing ocular lubrication. The surprising effectiveness of such low concentration is significant, because at these concentrations the incidence of patient complaints of ocular irritation attributable to the topical application of retinoids to the eye is expected to be much less.

The term "retinoid" as used herein is intended to include: retinoic acid (vitamin A acid) and its isomers, such as all-trans retinoic acid (tretinoin); retinol (vitamin A or vitamin A alcohol); and retinal (vitamin A aldehyde). The structure, physical properties and other characteristics of these compounds are described in *The Merck Index,* 10th Ed. (1983), and in numerous other publications cited therein; the contents of these publications which further describe retinoids and methods for preparing these compounds are incorporated herein by reference. This term is also intended to include near and remote analogues and functional derivatives of the above compounds which may be biotransformed into the active form (i.e., retinoic acid, retinol, or retinal), as well as all pharmaceutically acceptable salts of the foregoing compounds. Unless specifically indicated otherwise, any references to the term "retinoid" or variations thereof throughout the remainder of this specification are intended to include all such compounds.

Two problems associated with the formulation of compositions containing retinoids have been the poor solubility of these compounds and their generally crystalline form. The poor solubility of these compounds has represented a significant problem to be overcome when formulating ophthalmic compositions containing retinoids, since these compounds may cause a significant amount of ocular irritation when contacted with the eye in their undissolved crystalline form. In addition to this irritation problem, the poor solubility of these compounds may also frustrate or prevent the desired therapeutic effect, such as ocular lubrication, from being obtained.

It has been discovered that this solubility problem can be overcome by solubilizing the retinoids in corn oil or castor oil. This discovery is the subject of copending and commonly assigned U.S. patent application Ser. No. 711,345, filed Mar. 13, 1985.

The present invention is based in part on the discovery that the above-described problems associated with the formulation of ophthalmic compositions containing retinoids can also be overcome if the particle size of the retinoid crystals is reduced so that the majority of the particles have a maximum dimension (i.e., diameter) less than 20 microns, and preferably 90% or more of the particles have a maximum dimension less than 10 microns. Such microfine retinoid particles may be conveniently incorporated into various suitable ophthalmic vehicles without regard to the solubility of the retinoid.

Various known methods of particle size reduction may be utilized to reduce the size of the retinoid crystals. Examples of suitable methods include ball-milling, impaction micronization, and recrystallization. Examples of apparatus suitable for use in reducing the particle size of retinoid crystals include: the Abbe Engineering Co. ball mill; the Fluid Energy Co. Jet-O-Mizer; and the Trost Equipment Co. Gem-T Jet Mill.

The microfine retinoid particles may be combined with various types of pharmaceutically acceptable ophthalmic vehicles. Examples of suitable vehicles include: substantially nonaqueous liquid vehicles; substantially nonaqueous semisolid vehicles; solid vehicles or devices; liquid and semisolid vehicles comprising oil or lipid material and a substantial amount of water in the form of a dispersion or mixture; aerosols; and substantially aqueous vehicles. These vehicles are described in greater detail in copending and commonly assigned U.S. patent application Ser. No. 711,424, filed Mar. 13, 1985, and in copending and commonly assigned U.S. patent application Ser. No. 711,550, filed Mar. 13, 1985; the entire contents of these copending applications are incorporated herein by reference.

The only limitations with respect to the use of particular ophthalmic vehicles are that these vehicles be compatible with the retinoids contained therein and facilitate the above-described utility of the present compositions in treating dry eye syndrome and related ophthalmic surface disorders and providing topical ocular lubrication.

The compositions of the present invention are preferably based on either substantially nonaqueous semisolid vehicles or substantially aqueous vehicles. These preferred classes of vehicles are described in greater detail below.

The substantially nonaqueous semisolid class of vehicles utilized in the present invention may be generally described as comprising ointments. Specific examples of suitable vehicles in this class include: various types of petrolatum, such as white, yellow, red and so on; lanolin and lanolin derivatives; gelled mineral oil having a hydrocarbon base, such as PLASTIBASE TM; petrolatum and ethylene carbonate mixtures; petrolatum in combination with surfactants and polyglycol, such as polyoxyl 40 stearate and polyethylene glycol; and combinations of the foregoing vehicles. These vehicles may be combined with oils and/or waxes to vary consistency. The microfine retinoid particles may be uniformly dispersed in the above-described vehicles using conventional dispersion techniques.

The substantially aqueous class of vehicles utilized in the present invention includes the following types of vehicles: aqueous solutions which optionally contain cosolvents such as glycols and surfactants; aqueous solutions of the type just described which further comprise viscosity building agents, such as methylcellulose, polyvinyl alcohol (PVA), Carbopol, and so on; and medium to high viscosity polymer-based gels which increase the ocular residence time of the vehicle, such as gels based on Carbopol, cellulosics, and combinations thereof. The preferred vehicles of this class are based on polyanionic polymers; such vehicles are described in greater detail in the above-cited U.S. patent application Ser. Nos. 700,861 and 695,364, the entire contents of which have been incorporated herein by reference. The viscous gels and solutions described in these applications are based on polyanionic polymers having a molecular weight of from about 400,000 to about 6,000,000. These polymers may be further characterized as carboxyl vinyl polymers having carboxylic functional groups and preferably containing 2 to 7 carbon atoms per functional group. Preferred polymers of this class include Carbomers, available under the trade name Carbopol from the B. F. Goodrich Company. The known and readily available polymers Carbopol 934, 934P and 940 are specifically preferred. Such polymers are used in the viscous solution and gel preparations of the present invention at a level of from about 0.05% to about 8% by weight. More particularly, the concentration of these polymers in the viscous solutions of this invention is preferably from about 0.05% to about 0.25% by weight, while the concentration of these polymers in the gels of this invention is from about 0.25% to about 8% by weight. The microfine retinoid particles may be uniformly dispersed in the abovedescribed substantially aqueous vehicles using conventional dispersion techniques.

The stability of the retinoids contained in the compositions of the present invention is generally enhanced when antioxidants and/or opaquing agents are added to the preparations. It is therefore preferred that such stabilizing agents be added to the preparations. The compositions of the present invention preferably contain an antioxidant to protect the retinoid component of the compositions from oxidative degradation. Examples of suitable antioxidants include: propyl gallate, butylated hydroxyanisole (BHA), butylated hydroxytoluene (BHT), hydroquinone, ascorbyl palmitate, acetyl cysteine, ascorbic acid, nordihydroguaiaretic acid (NDGA), sodium bisulfite, and combinations thereof. The preferred antioxidants are propyl gallate, hydroquinone, BHT and BHA, with propyl gallate being particularly preferred. Such antioxidants are typically employed in an amount of from about 0.0005% to 1.0% by weight. The compositions of the present invention may also require an opaquing agent, since retinoids are generally photolytically reactive. Examples of suitable opaquing agents include: titanium dioxide and silicon dioxide. Such opaquing agents are typically employed in an amount of from about 0.01% to 1.0% by weight.

The compositions of the present invention which utilize polyanionic polymers as the vehicle preferably also contain a polymer stabilizing agent. The preferred stabilizing agents are polyols. These agents are utilized in an amount of from about 0.2% to 5% by weight. Representative examples of such polyols include: mannitol, sorbitol, glycerol, sucrose, related sugars, and the like. An especially preferred stabilizing agent is mannitol at a concentration of from 0.2% to 5% by weight.

The compositions of the present invention may also include conventional ingredients such as antimicrobial preservatives, neutralizing agents and tonicity agents, as described in more detail below.

Ophthalmic products are packaged in multiple use containers as a general rule. Preservatives may be included in the preparations of the present invention to prevent contamination of the preparations when they are exposed to microorganisms during use. Examples of suitable preservatives include: benzalkonium chloride, thimerosal, chlorobutanol, chlorhexidine, methylparaben, propylparaben, phenylethyl alcohol, sorbic acid, Onamer M (Onamer M is available from Onyx Chemical Company, Jersey City, N.J.), other agents known to those skilled in the art, and combinations thereof. Such preservatives are typically employed in an amount of from about 0.0005% to 1.0% by weight. If no preservative is desired, the preparations may be sterile packaged in unit-of-use containers. With respect to the use of Onamer M, the contents of commonly assigned U.S. Pat. No. 4,407,791 relating to the composition and ophthalmic use of Onamer M are incorporated herein by reference.

The compositions of the present invention which utilize substantially aqueous vehicles may be neutralized to the desired pH with basic chemicals such as sodium hydroxide, ammonium hydroxide, ethanolamine, urea, and selected amines. Mineral acids such as hydrochloric, phosphoric or sulfuric may be used to adjust pH toward acidity. The preferred pH range is from 4.5 to 8.5. The tonicity of such preparations can be adjusted to either hypotonicity, isotonicity or hypertonicity relative to normal tears by use of generally used materials known to the art. Sodium chloride and mannitol are preferred tonicity agents.

The mechanism of action which explains the utility of retinoids in the compositions of the present invention is not clear at this time. However, it has been found that the retinoids are effective in reversing keratinization and enhancing normal reepithelialization of the cornea.

The compositions of the present invention are useful as ocular lubricants and in the treatment of dry eye syndrome and related ophthalmic surface disorders. The dosage regimen utilized with the liquid formulations of the present invention is typically one or two drops dispensed from a standard ophthalmic dropping device, such as, glass or plastic dropping pipets or plastic bottles fitted with a dropper orifice. Individual drops are within the range of 5 to 75 mg. The drops are placed onto the corneal or scleral surface or into the lower conjunctival sac. The dosage regimen utilized with the solid and semisolid formulations is typically 5-75 mg, preferably 25-50 mg, placed into the lower conjunctival sac of the affected eye. Frequency of dosing is variably dependent upon the severity of the condition, but will typically be one to four times per day.

The compositions of the present invention contain an effective amount of retinoid to be dosed only at intervals sufficient to maintain the desired therapeutic effect. The dose and frequency will be critical to prevent a toxic effect. However, there may be a preferred dosage regimen wherein the retinoid provides remission and is no longer required, or is only required on a periodic prophylactic basis. It may be necessary in some cases to provide a separate product to dose the eye in between doses of retinoid so as to maintain the corneal epithelium in a hydrated state and provide additional lubrication, thereby reducing irritation and discomfort and enhancing tear film stability. This adjunctive product must be formulated so as to provide these beneficial effects while at the same time minimizing any potential toxicity to the somewhat compromised epithelial cells which could result from the usual preservatives contained in existing artificial tear products. It is therefore preferred to provide an adjunctive product in a sterile form but with no preservative. Another preferred method of providing the desired adjunctive product would be to use a low concentration of a preservative agent which has little or no surface activity, for example, a polyquat such as Onamer-M or similar polyquats. Onamer-M at a concentration of 0.001 wt. % is an effective preservative yet has almost no effect on the corneal epithelial cells. The adjunctive product would contain lubricating and mucomimetic polymers such as methylcellulose, dextran, polyvinylalcohol, polyvinylpyrrolidone, polyethylene glycol, carbomer, polyox, and particularly combinations thereof. These products could be dosed as frequently as required without any concern for adverse effects.

The following example is intended to further illustrate, but not to limit, the preparations of the present invention.

EXAMPLE

The following formulations (A and B) are representative of the compositions of the present invention which utilize substantially aqueous vehicles, particularly vehicles based on polyanionic polymers. All percentages are by weight based on the total weight of the preparation.

| Ingredients | Formulations | |
|---|---|---|
| | A | B |
| Tretinoin (micronized particles of all-trans retinoic acid) | 0.0005% | 0.005% |
| Propyl gallate | 0.005% | 0.005% |
| Benzalkonium chloride | 0.008% | 0.008% |
| Carbopol 940 | 0.2% | 3.0% |
| Mannitol | 5.0% | 0.5% |
| Sodium chloride | — | 0.4% |
| Edetate disodium | 0.01% | 0.01% |
| Hydrochloric acid and/or Sodium hydroxide | q.s. pH 7.2 | pH 7.2 |
| Purified water | q.s. 100 | 100 |

These formulations may be prepared as follows. First, the tretinoin is sterilized by dissolving it in a suitable solvent, such as diethyl ether, and filtering the resulting solution through a solvent-inert sterilizing membrane. Sterilized tretinoin crystals are then recovered from sterilized ethanol. The dried crystals are subjected to an aseptic particle size reduction treatment so that 90% or more of the resulting particles have a maximum dimension (i.e., diameter) of less than 10 microns. A slurry containing all ancillary ingredients is prepared by dispersing the Carbopol in 80% of the water until a uniform slurry is obtained, and then sequentially dissolving the remaining ingredients (not including tretinoin) in the Carbopol slurry. A small aliquot (i.e., about 10 wt. %) of this slurry is then utilized to disperse the comminuted tretinoin particles in a high shear mixer, such as a WARING ® blender. The resulting dispersion is then combined with the remainder of the slurry. The slurry is neutralized to pH 7.2 and the final volume if made up to 100% with purified water to form the viscous solution of formulation A or the viscous gel of formulation B.

The present invention has been described above in connection with certain preferred embodiments. However, as obvious variations thereon will become apparent to those skilled in the art, the invention is not to be considered as limited thereto.

What is claimed is:

1. A method of treating dry eye syndrome and related ophthalmic surface disorders, which comprises applying topically to the affected eye a therapeutically effective amount of a topical, ophthalmic pharmaceutical composition comprising: 0.00001% to 0.1% by weight of a retinoid selected from the group consisting of retinol, retinal, and retinoic acid and its isomers, said retinoid being in the form of microfine particles, the majority of said particles having a maximum diameter of less than 20 microns; and a pharmaceutically acceptable ophthalmic vehicle.

2. A method according to claim 1, wherein the composition further comprises 0.0005% to 1.0% by weight of an antioxidant selected from the group consisting of propyl gallate, hydroquinone, butylated hydroxytoluene, and butylated hydroxyanisole.

3. A method according to claim 1, wherein at least 90% of said particles have a maximum diameter of less than 10 microns.

4. A method according to claim 1, wherein the pharmaceutically acceptable ophthalmic vehicle comprises a nonaqueous semisolid vehicle selected from the group consisting of petrolatum; lanolin and lanolin derivatives; gelled mineral oil having a hydrocarbon base; petrolatum and ethylene carbonate mixtures; and petrolatum in combination with surfactants and polyglycol.

5. A method according to claim 1, wherein the pharmaceutically acceptable ophthalmic vehicle comprises an aqueous vehicle comprising 0.05% to 8% by weight of a carboxyl vinyl polymer having a molecular weight of from about 400,000 to about 6,000,000.

6. A method according to claim 5, wherein the carboxyl vinyl polymer is contained in the preparation in an amount of 0.05% to 0.25% by weight, and the preparation is a viscous solution.

7. A method according to claim 5, wherein the carboxyl vinyl polymer is contained in the composition in an amount of 0.25% to 8% by weight, and the preparation is a viscous gel.

* * * * *